United States Patent [19]

Lauterbach et al.

[11] Patent Number: 4,996,365
[45] Date of Patent: Feb. 26, 1991

[54] PREPARATION OF ALKYL-SUBSTITUTED CINNAMALDEHYDES

[75] Inventors: Gerald Lauterbach; Frank F. Pape, both of Ludwigshafen; Walter Gramlich, Heidelberg, all of Fed. Rep. of Germany

[73] Assignee: BASF Aktiengesellschaft, Ludwigshaften, Fed. Rep. of Germany

[21] Appl. No.: 401,241

[22] Filed: Aug. 31, 1989

[30] Foreign Application Priority Data

Sep. 17, 1988 [DE] Fed. Rep. of Germany ....... 3831713

[51] Int. Cl.$^5$ ............................................. C07C 45/00
[52] U.S. Cl. ..................................... 568/427; 568/450
[58] Field of Search ...................... 568/427, 450, 451

[56] References Cited

U.S. PATENT DOCUMENTS 2,976,321 3/1961 Dorsky et al. ....................... 568/427
4,749,814 6/1988 Chabardes ........................... 568/450

FOREIGN PATENT DOCUMENTS 267954 6/1927 United Kingdom ................ 568/427
1086447 10/1967 United Kingdom .

OTHER PUBLICATIONS

Chemical Abstract–10–Organic Chemistry 1951; p. 8997g.
Annales De Chimie 1967, pp. 243–249, Michel Barrelle, et al.
J. Amer. Chem. Soc. (1948) 70, p. 3953.
Houben–Weyl, Methoden der Organischen Chemie, Georg Thieme-Verlap, Stuttgart, New York, Band 6/lb, p. 959.
Houben–Weyl, band 7/1, p. 110 (1954).
J. Org. Chem. USSR, vol. 19, pp. 715–721 (1983).
Houben–Weyl, Methoden der Organischen Chemie, Georg Thyieme-Verlag, Stuttgart, vol. 7/1, p. 109 (1954).

Primary Examiner—Werren B. Lone
Attorney, Agent, or Firm—Oblon, Spivak, McClelland, Maier & Neustadt

[57] ABSTRACT

Alkyl-substituted cinnamaldehydes of the formula I

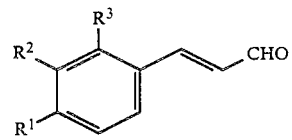

where one or more of $R^1$, $R^2$ and $R^3$ is alkyl of from 1 to 8 carbon atoms, preferably of from 1 to 4 carbon atoms, and non-alkyl $R^1$, $R^2$ and $R^3$ are each hydrogen, which comprises heating acetylene alcohols of the general formula II

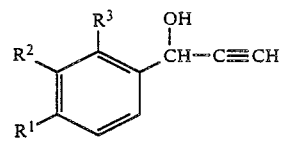

where $R^1$, $R^2$ and $R^3$ are each as defined above, in the presence of from 55 to 98% strength aqueous formic acid.

2 Claims, No Drawings

PREPARATION OF ALKYL-SUBSTITUTED CINNAMALDEHYDES

Substituted cinnamaldehydes are interesting intermediates not only for the synthesis of active substances but also for the preparation of scents. The scent industry is particularly interested in para-alkyl-substituted cinnamaldehydes, since they are ideal precursors for the corresponding, sought-after dihydrocinnamaldehyde scents (cf. GB No. 1,086,447). The most important substance within this class of substances is p-tert-butyldihydrocinnamaldehyde, which, being one of the most important lily of the valley scents, is used in large amounts in perfumery.

At present, alkyl-substituted cinnamaldehydes, in particular p-tert-butylcinnamaldehyde, are prepared by the aldol reaction from alkyl-substituted benzaldehydes and acetaldehyde (cf. U.S. Pat. No. 2,976,321). To minimize the self-condensation of acetaldehyde in this reaction and also to keep to a minimum further condensation reactions of the resulting cinnamaldehyde with acetaldehyde, it is necessary to carry out the reaction with an appreciable excess of the more costly reactant, namely the substituted benzaldehyde, and in high dilution (cf. U.S. Pat. No. 2,976,321).

A further method for preparing cinnamaldehydes is described in Ah. Org. Khim. 19(4) (1983), 808-15. This method comprises converting the acetylene alcohols which are readily available from the corresponding benzaldehydes into the desired cinnamaldehydes by rearrangement with poly(organovanadium)siloxanes. The disadvantages of this method are in particular the use of costly and difficult-to-obtain organovanadium-silicon compounds and the moderate yield of not more than 65%.

Good yields of unsubstituted cinnamaldehyde were obtained according to C.A. 1951, 8997 g, from phenylethynylcarbinol by slowly adding it dropwise to a mixture of water, sulfuric acid and a water-miscible solvent which does not contain any alcoholic OH groups, such as dioxane or acetic acid. The disadvantage here is that the workup of the reaction mixture is relatively complicated.

It is an object of the present invention to devise a process which avoids the disadvantages described and makes alkyl-substituted cinnamaldehydes available in good yield.

We have found that this object is achieved by a process for preparing an alkyl-substituted cinnamaldehyde of the general formula I

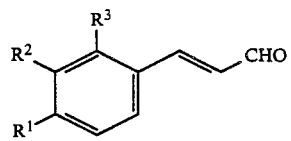

where one or more of $R^1$, $R^2$ and $R^3$ is alkyl of from 1 to 8 carbon atoms, preferably of from 1 to 4 carbon atoms, and non-alkyl $R^1$, $R^2$ and $R^3$ are each hydrogen, which comprises heating an acetylene alcohol of the general formula II

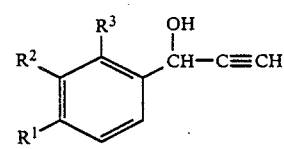

where $R^1$, $R^2$ and $R^3$ are each as defined above, in the presence of from 55 to 98% strength, preferably from 70 to 80% strength, aqueous formic acid.

It is true that the conversion of acetylene alcohols of the formula

in the presence of formic acid or the strongly acidic ion exchange material Dowex 50 was already known from Annales de Chimie 1967, 243-249, but only 2 out of 12 of the acetylene alcohols investigated gave α,β-unsaturated aldehydes - and this, what is more, only in unsatisfactory yields. The conversion of acetylene alcohols where R is an aliphatic or a cycloaliphatic radical only led to formates or acetates. The conversion of acetylene alcohols where R is o-hydroxyphenyl, p-methoxyphenyl or furyl only led to resins. Only the use of acetylene alcohols where R is phenyl or o-chlorophenyl gave the corresponding cinnamaldehydes in yields of from 53 to 60%.

It was accordingly likely that the conversion of acetylene alcohols of the general formula II using acidic catalysts such as formic acid would likewise give cinnamaldehydes only in poor yields, if at all.

A further prejudice against the advantageous process of the invention is evident from J. Amer. Chem. Soc. 70 (1948), 3953, where it is stated that Rupe's description of a rearrangement of tertiary acetylene alcohols into the corresponding α,β-unsaturated aldehydes by boiling with 85% strength aqueous formic acid could not be confirmed for aliphatic or cycloaliphatic acetylene alcohols. It is also stated that, although the odor of cinnamaldehyde was noticed on using phenylethynylcarbinol, the reaction essentially led to tarry products by polymerization.

In Houben-Weyl, Methoden der Organischen Chemie, Georg Thieme-Verlag, Stuttgart, New York, volume 6/lb, page 959, it is stated that the course of the Meyer-Schuster rearrangement

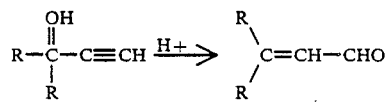

of ethynylcarbinols very much depends in detail on the substituents and the acidic reagent used, usually formic acid or sulfuric acid, and that esterifications, dehydrations and cleavage reactions are frequently occurring competitive reactions.

It is also stated in Houben-Weyl, volume 7/1, page 110, that it is only on heating arylethynylcarbinols with dilute acids that cinnamaldehydes are obtained, in yields of about 30%.

It is accordingly very surprising that the alkyl-substituted cinnamaldehydes of the general formula I can be obtained in very good yields by heating with acidic catalysts, in particular by heating with from 55 to 98% strength, preferably from 70 to 80% strength, formic acid. A particular surprise is the fact that under these drastic reaction conditions it is possible to convert even acetylene alcohols having the generally very acid-sensitive tertiary alkyl groups in the benzene ring, such as p-tert-butylphenylethynylcarbinol, into the desired p-tert-butylcinnamaldehyde in an 80% yield. Surprisingly, the cinnamaldehydes of the formula I are obtained in such high purity that they are easily convertible for example into the sought-after sensitive alkyl-substituted dihydrocinnamaldehyde scents.

Examples of acetylene alcohols of the general formula II which can be used are: p-tert-butylphenylethynylcarbinol, p-isopropylphenylethynylcarbinol and p-methylphenylethynylcarbinol.

Of particular importance is the conversion of p-tert-butylphenylethynylcarbinol and p-isopropylphenylethynylcarbinol.

The process according to the invention is carried out with aqueous formic acid as the acidic catalyst. The formic acid concentration can be varied within wide limits. At formic acid concentrations below about 55-60%, the conversion begins to decrease. In general, the formic acid can be employed in concentrations of about 55-98%. Concentrations of 70-80%, in particular of about 75%, have proved particularly advantageous. The formic acid is in general used in amounts of 200 to 800,° preferably about 400-550,% by weight based on the ethynylcarbinol of the formula II.

The process according to the invention permits an inexpensive and technically simple synthesis of important alkyl-substituted cinnamaldehydes of the formula I in high purity. The formic acid used in the rearrangement is easy to recycle by extracting the reaction mixture with a solvent, such as toluene, separating the phases, and reusing the recovered acid for the rearrangement. This ensures a minimum of waste. The organic phase is simply distilled to isolate the alkyl-substituted cinnamaldehydes in high purity.

EXAMPLE 1

A mixture of 250 g of 75% strength aqueous formic acid and 50 g of p-tert-butylphenylethynylcarbinol and 0.5 g of hydroquinone (as antioxidant) is refluxed for one hour. After the reaction mixture has cooled down, it is extracted twice with 250 ml of toluene each time. The aqueous phase is separated off and reused in a subsequent batch. The organic phase was washed with NaHCO$_3$ solution, concentrated and then distilled. This gave 40.5 g of p-tert-butylcinnamaldehyde having a boiling point of 95°-102° C./0.02 mbar (corresponding to a yield of 80% of theory).

EXAMPLE 2

A mixture of 250 g of 75% strength aqueous formic acid, 50 g of p-isopropylphenylethynylcarbinol and 0.5 g of hydroquinone is refluxed for 1 hour and then worked up as described in Example 1 to give 38 g (corresponding to 76% of theory) of p-isopropylcinnamaldehyde having a boiling point of 90°-95° C./0.06 mbar.

EXAMPLE 3

A mixture of 250 g of 75% strength aqueous formic acid, 50 g of p-methylphenylethynylcarbinol and 0.5 g of hydroquinone is refluxed for 1 hour and then worked up as described in Example 1 to give 40 g (corresponding to 80% of theory) of p-methylcinnamaldehyde having a boiling point of 90°-95° C./0.1 mbar.

We claim:

1. A process for preparing an alkyl-substituted cinnamaldehyde of the formula I

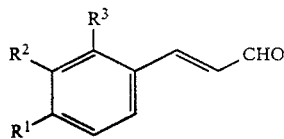

where one or more of $R^1$, $R^2$ and $R^3$ is alkyl of from 1 to 8 carbon atoms and non-alkyl $R^1$, $R^2$ and $R^3$ are each hydrogen, which comprises refluxing a mixture of an acetylene alcohol of the general formula II

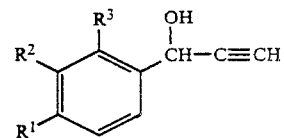

where $R^1$, $R^2$ and $R^3$ are each as defined above, and from 55 to 98% strength aqueous formic acid.

2. A process as claimed in claim 1, wherein said refluxing is carried out in the presence of from 70 to 80% strength aqueous formic acid.

* * * * *